US006316215B1

(12) United States Patent
Adair et al.

(10) Patent No.: US 6,316,215 B1
(45) Date of Patent: *Nov. 13, 2001

(54) METHODS OF CANCER SCREENING UTILIZING FLUORESCENCE DETECTION TECHNIQUES AND SELECTABLE IMAGER CHARGE INTEGRATION PERIODS

(76) Inventors: Edwin L. Adair, 317 Paragon Way, Castle Pines Village, CO (US) 80104; Jeffrey L. Adair, 1861 E. Redfox Pl., Highlands Ranch, CO (US) 80126; Randall S. Adair, 3082 S. Flamingo Way, Denver, CO (US) 80222

( * ) Notice: Subject to any disclaimer, the term of this patent is extended or adjusted under 35 U.S.C. 154(b) by 0 days.

This patent is subject to a terminal disclaimer.

(21) Appl. No.: 09/586,768

(22) Filed: Jun. 1, 2000

Related U.S. Application Data (63) Continuation-in-part of application No. 09/472,945, filed on Dec. 27, 1999, now Pat. No. 6,190,877.

(51) Int. Cl.[7] ............................... C12Q 1/02; C12Q 1/00; G01N 33/53

(52) U.S. Cl. ................... 435/29; 435/968; 435/4

(58) Field of Search .................. 435/29, 968, 4

(56) References Cited

U.S. PATENT DOCUMENTS

| 3,394,369 | 7/1968 | Rebeiz ............................ 47/58 |
| 3,846,490 | 11/1974 | Aronova et al. .................. 562/567 |
| 3,973,129 | 8/1976 | Blumberg et al. ............... 250/461 B |

(List continued on next page.)

FOREIGN PATENT DOCUMENTS 0 277 837  8/1988  (EP).

OTHER PUBLICATIONS

Abstract, Mu Y, et al., "P–S–D–007 Luminescence in the Diagnosis of Exfoliative Cells from Malignant Tumors", X–P–0021614131, vol. 9, No. 4, 1987, pp. 258–259.

Abstract, Schwartz, G., et al., "Selected Amino Acridines as Fluorescent Probes in Cytochemistry in General and in the Detection of Cancer Cells in Particular", *Analytical and Quantitative Cytology*, vol. 4, No. 1, 1982, pp. 44–54.

(List continued on next page.)

Primary Examiner—Louise N. Leary
(74) Attorney, Agent, or Firm—Sheridan Ross P.C.

(57) ABSTRACT

The methods of cancer screening allow for a safe, reliable, inexpensive and minimally invasive diagnosis. Cells are first collected through non-invasive or minimally invasive means. The collected cells are stored in a cell culture media. A chemical compound such as 5-ALA is introduced to the cultured cells. The cells are incubated a period of time to allow interaction between the introduced chemical compound and the collected cells. The cells are then studied under a fluorescence microscope which emits a specific frequency of light matching the excitation frequency of fluorescing abnormal cells. Pre-malignant and malignant cells will fluoresce while normal healthy cells generally will not fluoresce. In lieu of or in addition to observing the cells by the fluorescence microscope, an imager may be used to observe the cells wherein the imager includes selectable and variable charge integration capability. Observable fluorescence can be maximized by selecting the appropriate integration period. If necessary, the collected cells may be passed through a flow cytometer to more easily identify the fluorescing cells. A presumptive diagnosis of cancer may be made based upon the presence or absence of fluorescing cells. If a cell sample is adequately concentrated, a cell sorter is not needed, and the cell sample may be adequately viewed under the fluorescence microscope. Specific techniques are disclosed for non-invasive and minimally invasive cell collection. Each of these techniques minimize patient trauma by not requiring forced tissue removal as occurs in traditional biopsy procedures. A method of fluorescence guided endoscopy is also disclosed utilizing an imager with variable charge integration capability.

17 Claims, 5 Drawing Sheets

U.S. PATENT DOCUMENTS

| | | | |
|---|---|---|---|
| 4,772,691 | 9/1988 | Fukuda et al. | 540/145 |
| 4,897,444 | 1/1990 | Brynes et al. | 525/54.1 |
| 4,905,670 | 3/1990 | Adair | 128/18 |
| 4,920,143 | 4/1990 | Levy et al. | 514/410 |
| 4,977,177 | 12/1990 | Bommer et al. | 514/410 |
| 4,977,639 | 12/1990 | Aizawa et al. | 424/9 |
| 5,026,368 | 6/1991 | Adair | 606/15 |
| 5,043,101 | 8/1991 | Gordon | 252/408.1 |
| 5,079,262 | 1/1992 | Kennedy et al. | 514/561 |
| 5,087,636 | 2/1992 | Jamieson et al. | 514/410 |
| 5,117,466 | 5/1992 | Buican et al. | 382/6 |
| 5,122,453 | 6/1992 | Martin et al. | 435/7.24 |
| 5,143,054 | 9/1992 | Adair | 128/18 |
| 5,149,708 | 9/1992 | Dolphin et al. | 514/410 |
| 5,211,938 * | 5/1993 | Kennedy et al. | 424/7.1 |
| 5,234,940 | 8/1993 | Kennedy et al. | 514/410 |
| 5,251,613 | 10/1993 | Adair | 128/6 |
| 5,270,171 | 12/1993 | Cercek et al. | 435/29 |
| 5,283,255 | 2/1994 | Levy et al. | 514/410 |
| 5,308,608 | 5/1994 | Dolphin et al. | 424/9 |
| 5,418,169 | 5/1995 | Crissman et al. | 436/94 |
| 5,422,093 | 6/1995 | Kennedy et al. | 424/9.61 |
| 5,441,531 | 8/1995 | Zarate et al. | 607/90 |
| 5,554,505 | 9/1996 | Hajek et al. | 435/721 |
| 5,556,764 | 9/1996 | Sizto et al. | 435/7.24 |
| 5,605,805 | 2/1997 | Verwer et al. | 435/7.24 |
| 5,616,342 | 4/1997 | Lyons | 424/450 |
| 5,627,040 | 5/1997 | Bierre et al. | 435/7.24 |
| 5,652,114 | 7/1997 | Chu et al. | 435/7.23 |
| 5,773,609 | 6/1998 | Robinson et al. | 540/145 |
| 5,955,490 | 9/1999 | Kennedy et al. | 514/410 |

OTHER PUBLICATIONS

Abstract, Gardiner, R.A., et al., "Abnormal prostatic cells in ejaculates from men with prostatic cancer: A preliminary report", *British Journal of Urology*, vol. 78, No. 3, 1996, pp. 414–418.

Abstract, Bologna, M., et al., "Improved tissue culture method for the study of prostatic carcinoma: A significant diagnostic tool", *Pathology Research and Practice*, vol. 191, No. 9, 1995, pp. 899–903.

Abstract, Sauter, E.R., et al., "Nipple aspirate fluid: A promising non–invasive method to identify cellular markers of breast cancer risk", *British Journal of Cancer*, vol. 76, 1997, pp. 494–501.

Abstract, Suglyama, M., et al., "Non–invasive detection of bladder cancer by identification of abnormal CD44 proteins in exfoliated cancer cells in urine", Abstract, *Clinical Molecular Pathology*, 1995, vol. 48, pp. M142–M147.

Nyamekye, I., et al., "Photodynamic Therapy of Normal and Balloon–Injured Rat Carotid Arteries Using 5–Amino–Levulinic Acid", *Circulation*, vol. 91, No. 2, Jan. 15, 1995, pp. 417–425.

Peng, Q., et al. "5–Aminolevulinic Acid–Based Photodynamic Therapy", *American Cancer Society*, 1997, pp. 2282–2305.

Berg, K., et al., "The influence of iron chelators on the accumulation of protoporphyrin IX in 5–aminolaevulinic acid–treated cells", *British Journal of Cancer*, 1996, pp. 688–697.

Noodt, BB, et al., "Apoptosis and necrosis induced with light and 5–aminolaevulinic acid–derived protoporphyrin IX", *Flow Cytometry*, 1996, pp. 22–29.

Malik, Z, et al., "Destruction of erythroleukaemic cells by photoactivation of endogenous porphyrins", *British Journal of Cancer*, 1987, 56, pp. 589–595.

Abstract; Leunig–A., et al., "Fluorescence Photodetection of Neoplastic Lesions in the Oral Cavity Following Topical Application of 5–Aminolevulinic Acid", *Laryngo–Rhino–Otologie*, vol. 75, No. 8, Aug. 1996, pp. 459–464.

* cited by examiner

Fig-1

Fig_2A

Fig-3

Fig_4

METHODS OF CANCER SCREENING UTILIZING FLUORESCENCE DETECTION TECHNIQUES AND SELECTABLE IMAGER CHARGE INTEGRATION PERIODS

This application is a continuation-in-part of U.S. patent application Ser. No. 09/472,945 filed on Dec. 27, 1999 now U.S. Pat. No. 6,190,877 entitled "Method of Cancer Screening Primarily Utilizing Non-Invasive Cell Collection and Fluorescence Detection Techniques."

TECHNICAL FIELD

This invention relates to methods of cancer screening and, more particularly, to methods primarily utilizing non-invasive cell collection techniques, and fluorescence detection techniques for positive identification of malignant cells.

BACKGROUND ART

There are a number of prior art methods and apparatuses which are used in the detection and treatment of cancer. Fluorescent markers have been used to help identify cancerous tissue within a patient. There are also a number of prior art methods and apparatuses which relate to flow cytometry and the act of segregating and counting malignant cells within a tissue sample. One example of a prior art reference which discloses the use of fluorescence detection for cancer screening is U.S. Pat. No. 5,270,171 to Cercek, et al. This reference teaches a method to identify, separate and purify the factor or factors that provoke a response by SCM (structuredness of the cytoplasmic matrix) responding lymphocytes. The use of such purified factor or factors enhances a SCM cancer screening test. The SCM is a peptide of at least nine amino acid residues. The residues produce at least a 10% decrease in the intracellular fluorescence polarization value of SCM responding lymphocytes from donors afflicted with cancer. Antibodies specific for the SCM factor are useful in immunoassays that can detect the factor, including detection of cancer cells grown in vitro. The SCM factor is useful for screening of blood samples and other body fluids or cell aspirates for the presence of malignancy in the donor. A method is also disclosed for testing lymphocytes obtained from the donor for presence or absence of a malignancy. A further method is also disclosed for screening a blood sample for the presence of a malignancy in a body of a donor.

U.S. Pat. No. 5,554,505 to Hajek, et al. discloses an optical screening method and apparatus for identifying both the morphology and selective characteristics or properties expressed by cells, such as cancer cells. Cell samples are combined with one or more sets of microspheres, each set having a reactant bonded thereto which will bind the microspheres to a specific molecule which can exist on one or more types of cancer cells. The cells and microspheres are formed as a smear on a slide, stained with a histological type stain and optically viewed to identify the type of cells to which the different set of microspheres do or do not bind. A quick cancer screening method is provided by adding selected sets of microspheres comprised of unique reactants to different sample smears of cells, and optically screening the sample smears for interaction with the microspheres.

U.S. Pat. No. 5,562,114 to Chu, et al. discloses a diagnostic immunoassay method using monoclonal antibodies. These monoclonal antibodies are capable of identifying an antigen associated with carcinomas of ductal lineage and can be used both diagnostically and therapeutically. More specifically, the monoclonal antibodies of this reference are capable of targeting the breast carcinoma cells in vivo. The monoclonal antibodies are purified and are labeled with radioactive compounds, for example, radioactive iodine, and then are administered to a patient intravenously. After a localization of the antibodies at the tumor site, they can be detected by emission, tomographical and radionuclear scanning techniques thereby pinpointing the location of the cancer.

U.S. Pat. No. 5,087,636 to Jamieson, et al. discloses a method to identify and destroy malignant cells in mononuclear cell populations. This method includes the steps of contacting a composition of bone marrow cells or other cells with a green porphyrin of a specific compound, irradiating the cell composition with light at a wave length effective to excite fluorescence of the green porphyrin, and then detecting the presence or absence of fluorescence indicating malignancy. This reference also discloses the steps by which the bone marrow cells are removed, separated, washed and diluted to an appropriate concentration for treatment, incubated, centrifuged, and exposed to the irradiating light.

U.S. Pat. Nos. 5,308,608 and 5,149,708 to Dolphin, et al. disclose specific types of porphyrin compounds which may be used for detection, photosensitization, or the destruction of a targeted biological material when the targeted tissue is contacted with the specified porphyrin, and irradiated with light that excites the compound.

U.S. Pat. No. 5,211,938 to Kennedy, et al. discloses a method of detection of malignant and non-malignant lesions by photochemotherapy of protoporphyrin IX precursors. 5-amino levulinic acid (5-ALA) is administered to the patient in an amount sufficient to induce synthesis of protoporphyrin IX in the lesions, followed by exposure of the treated lesion to a photoactivating light in the range of 350–640 nanometers. Naturally occurring protoporphyrin IX is activatable by light which is in the incident red light range (600–700 nanometers) which more easily passes through human tissue as compared to light of other wave lengths which must be used with other types of porphyrins. In short, the use of 5-ALA makes cell fluorescence easier to observe, and also greatly reduces the danger of accidental phototoxic skin reactions in the days following treatment since protoporphyrin IX precursors have a much shorter half life in normal tissues than other popularly used porphyrins.

Another set of references exists which relate to flow cytometry utilizing fluorescence producing compounds. One such prior art reference includes U.S. Pat. No. 5,605,805 to Verwer, et al., which discloses a method for determining the lineage of acute leukemia cells in the sample by fluorocytometry. Other examples of fluorocytometry utilizing fluorescence include U.S. Pat. Nos. 5,418,169 to Crissman, et al., U.S. Pat. No. 5,556,764 to Sizto, et al., and U.S. Pat. No. 5,627,040 to Bierre.

Present methods relating to cancer screening using fluorescence detection systems require the use of interventional devices such as endoscopes which have the special capability of delivering specified light frequencies to a targeted area within a patient. These endoscopes illuminate the targeted part of the body in which cancer is suspected. The light delivered at a specified frequency illuminates an area which has previously been subjected to some type of fluorescent marker, such as a porphyrin which causes malignant cells to illuminate or fluoresce under observation of light at a specified frequency. In all cases, introduction of an endoscope into the body requires some type of sedation or general or local anesthesia. Once a tumor has been located by use of the interventional device, depending upon the type of tumor, photochemotherapy or other treatment means can be used. However, prior to actual treatment, there must be a confirmed test of cancer. Accordingly, the tumor still needs to be sampled by an appropriate biopsy method. Generally, biopsy methods also require some type of sedation or anesthesia. Thus, traditional methods of confirming a malignancy may require at least two interventional surgical procedures.

While each of the foregoing references may be adequate for their intended purposes, many of these inventions require surgical techniques to remove the cell samples which can be traumatic to the patient. Furthermore, many of the references require complex equipment, and special medical expertise in order to conduct the procedures and to make the diagnoses. Therefore, there is a need for a reliable cancer screening technique or method which can test for cancer in a wide variety of cells and which may be accomplished by non-invasive or minimally invasive cell collection techniques which limit patient trauma, are inexpensive to conduct, and can be confirmed positively by a pathologist, oncologist or other physician without additional testing or screening. The invention described below provides each of these advantages, among others, which will be apparent to those skilled in the art.

DISCLOSURE OF THE INVENTION

The present invention relates to methods of cancer screening utilizing non-invasive or minimally invasive cell collection techniques, and fluorescence detection techniques. The term "non-invasive" as used herein and as applied to a specific cell collection technique shall mean cell collection which does not involve the forced removal of tissue as by the act of cutting or otherwise tearing away cell tissue which would normally remain attached to the body. As discussed further below, a cell collection technique using a cytological brush would be considered non-invasive because, although contact is made with a targeted area of tissue to be removed, the cytological brush simply removes a top layer(s) of cells which would normally exfoliate or desquamate from the body. Thus, a cytological brush used according to the cell collection techniques of this invention does not involve the scraping of tissue to a degree that it cuts or tears tissue away from the body. The term "minimally invasive" as used herein and as applied to other cell collection techniques disclosed herein shall mean the removal of cells from the body which requires some interventional means for accessing the targeted group of cells, but does not require the actual tearing or cutting away of such targeted tissue. As discussed further below, minimally invasive cell collection techniques include the use of a fine gauge needle or catheter which must penetrate the body to gain access to interior targeted tissue. This minimally invasive cell collection technique is used specifically with the collection of cells from the central nervous system, peritoneal cavity, and thoracic cavity. Cell collection from these areas in the body is not achieved by cutting or tearing away the tissue, but is achieved by non-invasive means once the minimally invasive access procedure has taken place.

Thus, according to one aspect of the present invention, the exfoliation or dislodgement of cells from the human body is achieved through non-invasive means. For dislodgement of pulmonary system cells, techniques are disclosed which include fist percussion while a patient is placed in a postural drainage position. For exfoliation of gastrointestinal cells, the techniques include lavage cytology by oral administration of a first balanced electrolyte solution to cleanse the bowel which is followed by oral administration of an additional electrolyte solution to produce a clear anal effluent for cytologic evaluation. Cells in the oral cavity may be collected by a cytological brush. For prostate gland cell dislodgement, a physician may "milk" the prostate to express contained fluids which are carried through the ductal system to the urethra via the seminal vesicles and the ejaculatory ducts. For urinary tract cells, exfoliation may be achieved by rapid oral fluid intake and the use of a diuretic such as Lasix™. For collection of cervical and uterine cell samples, a cytological brush may also be used. For breast cell collection, the ductal system of the breast may be opened by the use of a product such as Seruminex™ which dissolves "plugs" in the ducts of the nipple, and gravity is allowed to cause fluids to drain out. The discussion below more fully details these special non-invasive cell collection techniques. Collection of other cell types is also discussed below.

Once the targeted cells have been removed from the body, they are immediately placed in a temperature controlled (37° C.) cell culture solution or media to keep them alive a desired period of time. For most cells, a cell transport media is used which is identical to commercially available cell culture media. A water bath is typically used to maintain the culture at the desired temperature.

A photosensitive compound is then introduced to the cell culture. These compounds when administered in appropriate amounts selectively enter into pre-malignant and malignant cells, and provide a "fluorescent marker" in the cells, primarily in the mitochrondia surrounding the nucleus. The compounds which may be used in this method to induce fluorescence include 5-ALA, protopoiphyrin IX, tetrakis carboxy-phenyl porphine (TCPP), hematoporphyrine derivative, photofrin, and photofrin II and other known in the art to cause fluorescence in pre-malignant or malignant cells. For TCPP, this compound enters live cells via a special transport mechanism found in the outer cellular wall. TCPP will not enter dead cells, thus making it important that a live cell culture be maintained. Once inside the cell, TCPP appears to migrate to the perinuclear areas and become involved with the mitochrondia. In short, the above compounds will cause pre-malignant or malignant cells to fluoresce when exposed to frequencies of light which match the excitation frequency of the particular compound used; however healthy cells will generally not fluoresce.

Once the photosensitive compounds are introduced to the cell culture, they are allowed to interact with the cell tissue a specified amount of time in a controlled environment. After this incubation period, cells may be examined by use of a fluorescence microscope to see if any cells fluoresce. Fluorescence in the cell indicates a high degree of suspicion for malignancy. The cell culture can first be centrifuged to help separate the cells from the cell culture fluids. The cells are resuspended in saline, and a small aliquot is placed on a slide. If no cells are found to fluoresce after initial observation under the fluorescence microscope, the cells are disaggregated and processed through a flow cytometer utilizing fluorescence detection. This is done to ensure that no fluorescent cells are overlooked. Manual examination of cell suspensions is not particularly accurate, since millions of cells need to be examined. Flow cytometers can find a single fluorescent cell in a field of millions of cells with virtual 100% accuracy. The fluorescence microscope and the flow cytometer provide light to match the excitation frequency of the particular compound used. For example, the excitation frequency for TCPP is approximately 380–450 nanometers. If fluorescent malignant cells are found by the fluorescence microscope, they may also be counted and disaggregated for further study. After incubation, no further care of the cell specimen is required.

Alternatively, the above-described photosensitive compounds may be administered directly to the patient prior to cell collection. 5-ALA can be administered orally, topically, or parenterally (by injection); however, the other compounds have to be administered topically or by injection (parenterally). The waiting period prior to cell collection is then two to four hours, depending upon the compound introduced. After sufficient time has been provided for interaction between the compound and the targeted cells, the cells may then be exfoliated or dislodged from the patient through non-invasive or minimally invasive techniques.

Also in accordance with the methods of this invention, it is contemplated that additional means may be used to examine the cell culture to provide enhanced capability to observe fluorescence. Specifically, variable charge integration capable imagers including CMOS and CID type imagers may be used in conjunction with, or even separate from, a fluorescence microscope to determine if any cells fluoresce. CID and CMOS imagers have variable charge integration capabilities which allow these types of imagers to provide images which are manipulated by selected charge integration periods. Particularly for weak fluorescence in a cell culture which may only have a handful of malignant cells, it is very difficult to find such cells solely by the fluorescence microscope. Although this small number of cells would be separated and observed by use of a flow cytometer utilizing fluorescence detection, it is still advantageous to have the capability to find and view such malignant cells without having to conduct flow cytometry. Since flow cytometry requires the use of expensive equipment, the use of CID and CMOS type imagers would enhance the capability of outpatient clinics to effectively screen for cancer and would minimize the need for use of a flow cytometer and associated equipment. Some commercially available fluorescence microscopes have CCD type imagers which are not capable of variable charge integration. CCD imagers are charge storage and transfer devices wherein the detector signal produced is representative of the total light impinging or falling upon the pixel array during a preset exposure time. Because of the construction of CCD devices, these exposure times cannot be manipulated for charge integration because CCD imagers have destructive readout. In other words, each charge is read by transferring the collected charge in each pixel in a serial fashion to a readout amplifier. The same photon generated charge collected at the pixel site is transferred (coupled) pixel by pixel one at a time in a predesignated sequence that cannot be interrupted. When the pixel charge sequence is transferred to the readout amplifier, the pixel charge is destroyed. For CID (charge injection device) imagers, pixels accumulate charge which is injected into the substrate. Pixels in CID imagers can be individually accessed; however, in doing so, the charge is not destroyed by actual charge transfer, but is sensed and then replaced so that the integration process is not disturbed. Light continues to be collected for the preset integration period while the pixels continue to be monitored. This non-destructive readout capability of CID imagers makes it possible to carry out real time exposure monitoring and it also allows integration periods to be varied such that longer integration periods represent greater amounts of light being collected in the pixels. By having the capability to adjust the integration periods, fluorescence detection can be enhanced by choosing an integration time which maximizes observable fluorescence. CMOS imagers also have variable charge integration capability to enhance observed fluorescence. As with CID imagers, integration periods in CMOS imagers may be varied, and fluorescence detection can be enhanced by choosing an integration period which maximizes the same. Two examples of CMOS imagers which may be incorporated within the method of this invention are those disclosed in my earlier patents, U.S. Pat. Nos. 5,986,693 and 5,929,901. The disclosures of these patents are hereby fully incorporated herein by reference. These CMOS imagers, as well as commercially available CID imagers such as those manufactured by CIDTEC of Liverpool, N.Y. can be modified to include an imager integration time switch which allows an operator to preselect a desired integration period which maximizes observable fluorescence. This imager integration time select switch is coupled to video processing circuitry by clock select circuitry which varies the integration period as selected by the operator. Representative integration periods might include 250 milliseconds, 500 milliseconds, 2 seconds, 3 seconds and 5 seconds. The operator would adjust the integration periods to maximize the observed fluorescence. For example, an integration period selected at 5 seconds would result in charge being accumulated in the pixels of the imager for a 5-second period and, thus, the observed fluorescence intensity would be greatly magnified in comparison to standard readout cycles for CCD devices which may only be one-sixtieth of a second.

By the methods of this invention, quick and reliable means are provided for cancer screening. Because non-invasive or minimally invasive techniques are used for cell collection, patient trauma is reduced along with the cost of the procedure. Because the method of this invention provides the option of introducing the compounds ex-vivo, the concern for any possible allergic reaction or phototoxic reaction by a patient's exposure to the sun is eliminated. Furthermore, because no tissue biopsies are taken, the method of this invention eliminates the inherent hazard in administering local and/or general anesthesia. Cell marking by use of the above-identified compounds is extremely reliable in terms of differentiating healthy cells from pre-malignant or malignant cells. The segregation, counting and analysis of the fluorescent cells may be achieved with commercially available flow cytometers and supporting equipment. The results of the cancer screening procedure may be forwarded to a pathologist who may wish to conduct additional tests to further determine the exact nature of the malignancy. By the use of selected charge integration periods through a CID or CMOS type imaging device, this enhanced capability to observe fluorescence also aids the pathologist who ultimately makes the diagnosis of cancer. The fluorescing cells may be photographed to provide documentation of malignancy. These and other advantages are discussed more fully below in the detailed description taken in conjunction with the corresponding figures.

DETAILED DESCRIPTION OF THE INVENTION

Figure 1:
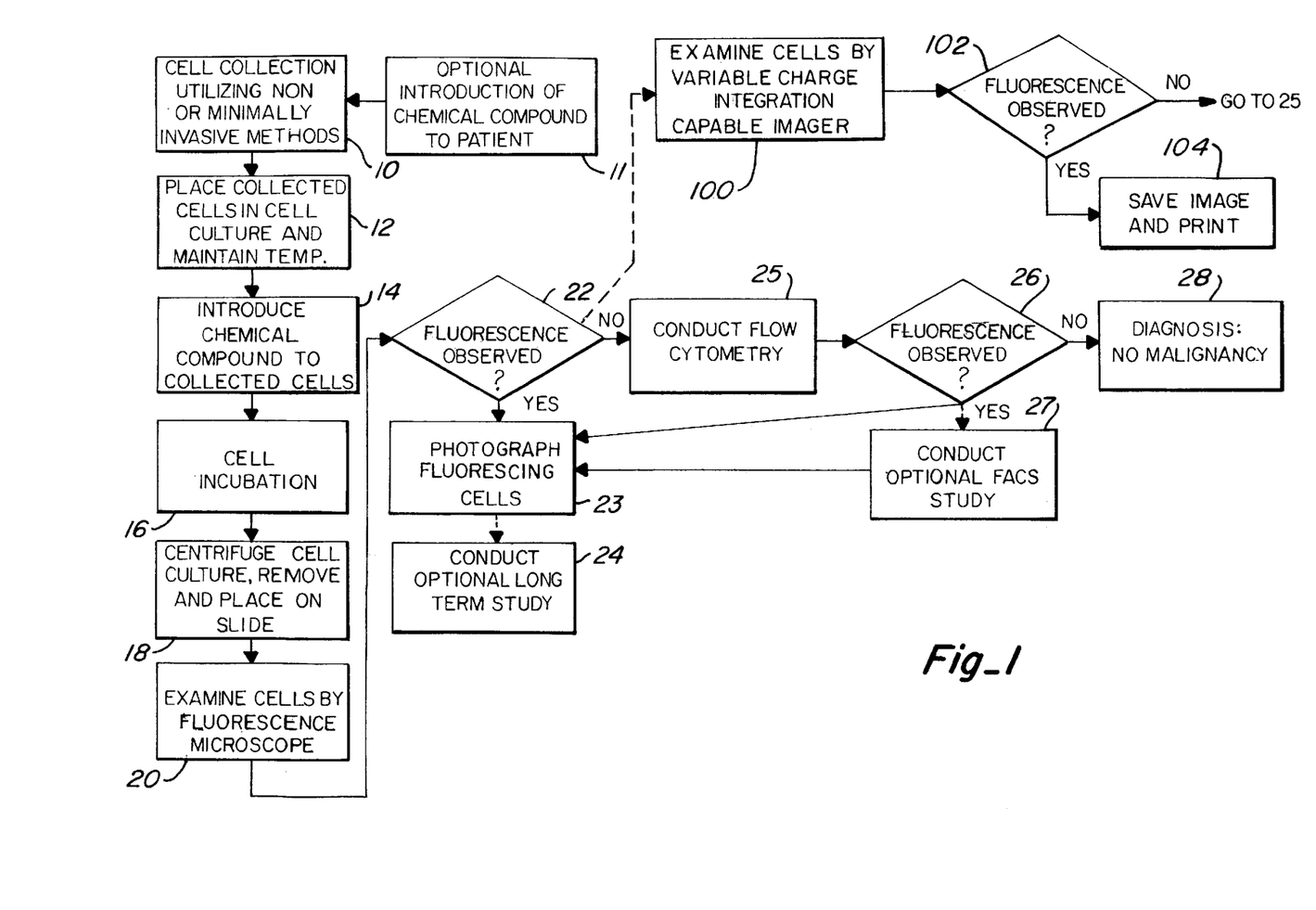
FIG. 1 is a simplified flow diagram illustrating the major steps in the methods of this invention.

FIG. 1 illustrates the major steps in the methods of this invention. As shown, the process begins with non-invasive means or minimally invasive means of cell exfoliation/collection 10. Once collected, the cells are then placed in a culture media or cell transport media, shown at step 12. The goal is to keep the collected cells alive and viable after removal from the body. Thus, even at this intermediate step, the cells should be maintained at approximately 37° C. by use of a water bath or other means. Next, the collected cells are exposed to a chemical which induces fluorescence in pre-malignant and malignant cells, illustrated as step 14. As discussed above, the chemical compounds which are contemplated for use in this invention include, but are not limited to, 5-ALA, protoporphyrin IX, TCPP, hematoporphyrin derivative, photofrin, and photofrin II. Other possible compounds which may be used include uroporphyrin; coproporphyren; tetraphenylporphinesulfonate (TPPS); and tetraporphen (4, N-methylpyridil) (TMPP). These compounds, when administered in appropriate amounts, selectively enter pre-malignant and malignant cells, and provide a fluorescent marker inside the cell, primarily in the mitochrondia surrounding the nucleus. Of special utility is the compound TCPP. This compound is available from Porphyrin Products, P.O. Box 31, Logan, Utah. As best understood, TCPP enters a live cell via a special cell transport mechanism in the outer cellular wall. TCPP will not enter a dead cell. Once inside the cell, the TCPP migrates to the perinuclear areas and becomes involved with the mitochrondia. TCPP is not a stain as used in a Pap smear or other similar procedures. Therefore, it is imperative that this compound be utilized for fluorescent tagging of cells prior to cell death. For ex-vivo introduction of the chemical compound, the preferred compound is TCPP.

In terms of cell storage in the culture media, commercially available cell culture media may be used to keep the cells viable. These solutions contain nutrient materials as well as selected antibiotics to counteract any infective organisms which might alter capabilities of the cell to effectively interact with the introduced chemical. Immediately after removal from the body, the cells are placed in the nutrient solution or cell transport media. For example, the cell samples may be placed in a commercial medium known as "Dulbecco's Modified Eagles Medium," which is supplemented with a 10% calf serum, penicillin and streptomycin at standard tissue culture concentrations. This medium is well known in cell culture laboratories and readily available commercially or may be formulated in the cell culture laboratory by technicians.

After introduction of the chemical to the cell culture, the culture is incubated for a specified amount of time which allows the live cells to absorb and interact with the compound, shown as step 16. In test trials, it has been found that a 1–4 hour incubation time is needed for pre-malignant and malignant cells to interact with the compounds. The average time for incubation for TCPP is 1–2 hours. The cells are maintained in a culture incubator by use of the water bath at approximately 37° C. The incubator may utilize air containing 5% carbon dioxide which surrounds the water bath. These cell suspensions contain both non-malignant, and (in some cases) malignant cells. Normal cells are difficult to keep alive in cell culture, and generally die in seven to 10 days from time of removal from the body regardless of the care taken in trying to maintain their survival. Malignant cells, on the other hand, can generally be kept alive in cell culture situations for several weeks or months. During this early incubation period, it is also advisable to agitate the cell cultures at frequent intervals to make sure that the compound comes into contact with all cells contained within the cell culture container.

After adequate interaction has occurred between the introduced chemical compound and the cells within the culture, the cells need to be prepared for first observation. Accordingly, the cell suspension is placed in a centrifuge tube and the cell sample is centrifuged. The cells become concentrated at the bottom of the centrifuge tube in a "button" of cells. The cell culture media fluid is then removed by pouring off all but about 10% of the fluid. The remaining cell culture media is then removed with a pipette, and the cells are resuspended in a saline solution. Small amounts of resuspended cells are then removed with a pipette (e.g., one to two gtts) and placed on a glass slide with a slide cover. These preparation efforts are generally indicated at block 18.

The cells are then observed under a fluorescence microscope. The fluorescence microscope can be tuned to provide light which matches the excitation frequency. For TCPP, the excitation frequency ranges from 380–400 nanometers. The technician observing the cells under the fluorescence microscope looks for cells which fluoresce in the visible red range (approximately 630 nanometers). The step of examining the cells and providing a matching excitation frequency for observation of characteristic fluorescence is shown at block 20. If a compound other than TCPP is used, the fluorescence microscope is tuned to provide the matching excitation frequency, and observation is made for the characteristic fluorescence. There are a number of commercially available fluorescence microscopes which may be used in the method of this invention. Some of the manufacturers of such devices include Olympus, Nikon, and Karl Zeiss. If any cells fluoresce, then this would be an indication of malignancy. This is shown at decision point 22 wherein the next step would be color photography of the fluorescing cells for documentation purposes, shown at block 23. Optionally, long-term cell observation could be conducted wherein the cells would be placed back into a culture media for additional studies. This is shown at block 24.

If no fluorescing cells were found with the initial observation under the fluorescence microscope at block 20, then, as also shown at decision block 22, the cells then undergo further analysis to determine whether there are any malignant cells present. Although the use of a fluorescence microscope would allow an observer to find larger numbers of malignant cells, this is not an absolute test for finding fluorescing cells. Accordingly, these cells would be processed through a flow cytometer to find and count fluorescing cells. This is shown at block 25. If the flow study reveals any fluorescing cells, this would be an indication of malignancy. As shown at block 27, the specimen could then prepared for fluorescence activated cell sorting. Fluorescence activated cell sorting (FACS) is done to further concentrate the specimen of fluorescing cells for easier observation and is an additional function which may be incorporated within a flow cytometer. Fluorescence activated cell sorting is achieved based upon the presence or absence of fluorescence by a particular cell. By use of one of the compounds discussed above, the cells which are pre-malignant or malignant will fluoresce while non-malignant cells will not. Accordingly, fluorescence activated cell sorting can effectively separate out in a very precise manner pre-malignant and malignant cells versus non-malignant cells. Once the FACS study is complete, the fluorescing cells are segregated from the remaining cells which do not exhibit fluorescence. This concentrated sample of fluorescing cells then may be viewed under a fluorescence microscope and photographed. The presence of even one fluorescing cell can be cause for making a screening diagnosis of cancer. If no fluorescing cells are found, then the screening diagnosis is no malignancy, shown at block 28. Optionally, a long-term study of the fluorescing cells found at block 25 may also be conducted.

FIG. 1 also shows optional step 100 wherein cells may be examined by a variable charge integration imager. If fluorescence is observed by the enhanced image created by the imager, as shown at step 102, then the image may be saved (e.g., on disk or other medium), and printed as shown at step 104. If there is still no fluorescence observed after examining the cells by the imager, then flow cytometry can be conducted, as shown at step 25, and the investigational procedure continued to find any fluorescing cells. It should also be understood that the cells can be examined with the imager at any time during the investigation, for example, once flow cytometry has been conducted, as well as after a FACS study has been conducted. Thus, the use of a variable charge integration imager at different points in the investigational procedure can enhance the ability to observe fluorescence.

Although the above procedure describes the step of conducting a FACS study, it should be understood that, in those instances in which no fluorescing cells are found under initial observation at block 20, a screening diagnosis of a malignancy can actually be made once the cells are processed through the flow cytometer and fluorescent cells are found and counted. As discussed above, the main reason that the FACS study is conducted is to better concentrate the fluorescing cells within a smaller sample size. Otherwise, finding the cells under the fluorescence microscope and photographing the cells would be much more difficult.

Figure 3:
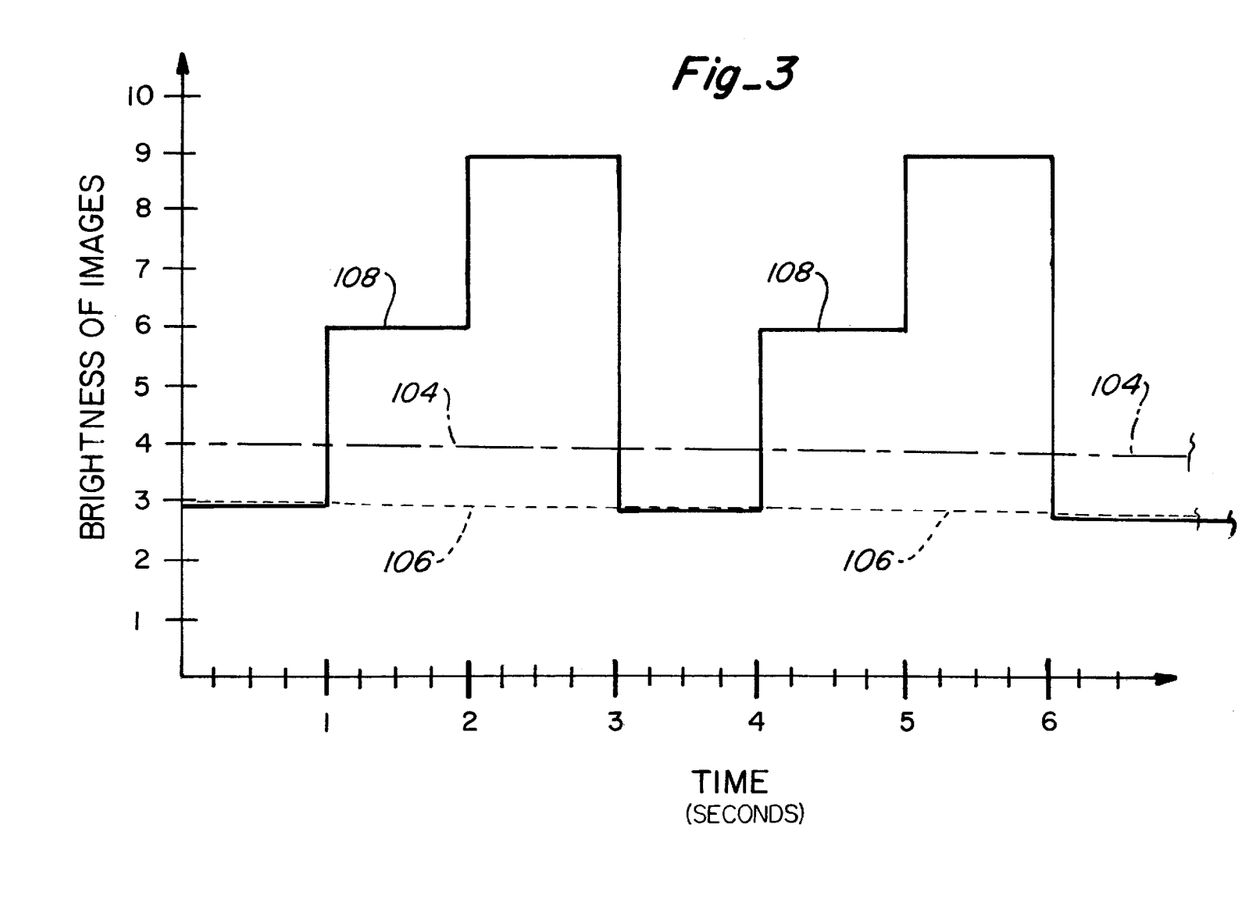
FIG. 3 is a graphical representation of how variable charge integration periods can enhance the capability to observe fluorescence in a particular cell culture.

As seen in FIG. 3, the intensity or brightness of observable fluorescence may be enhanced by a CID or CMOS imager which has a variable charge integration capability. The example at FIG. 3 shows a situation in which a cell culture may only emit an amount of light which is not normally capable of being seen by the human eye through a fluorescence microscope or may otherwise be very difficult to find. By adjusting the integration period, the image produced by the CID or CMOS imaging device intensifies the brightness or intensity of the fluorescence over the integration period to a much more readily observable amount of light. In the example of FIG. 3, the brightness of a particular image is measured on the vertical axis, while the time in which the image is viewed or observed is measured on the horizontal axis. A threshold level of observable fluorescence is shown at horizontal line 104, and which represents an average amount of fluorescence which can be observed by a commercially available fluorescence microscope without the aid of any special equipment. Any level of fluorescence falling below this threshold level 104 would be considered very difficult to observe. Dashed line 106 represents the level of fluorescence which may occur in a particular cell sample without the aid of viewing the cell sample by an imager having variable charge integration capability. Thus, this fluorescence 106 may still constitute a diagnosis of cancer; however, because of the low fluorescence, it may be very difficult, if not impossible, to find by use of the fluorescence microscope. In accordance with the methods of this invention, an imager having charge integration capability could be used to enhance or brighten the observable fluorescence. The observed fluorescence using such an imager is shown as line 108. As shown, a three-second integration period has been chosen. During the first second of observation, there is no observable difference between viewing the cell sample by use of a CCD type imager versus viewing the cell sample with the aid of an imager having charge integration capability. However, between one and two seconds, the observed fluorescence 108 is now above the threshold level 104 which makes the fluorescing cells much more easier to locate and view. Between two and three seconds, the image is further brightened or enhanced due to the continuing charge integration period wherein charge continues to accumulate in the pixels of the imager. The stepped pattern of observed fluorescence 108 is due to the monitor update cycle or period. Thus, between one and two seconds, a first update of the monitor period occurs which reflects the increased charge accumulating in the pixels of the imager. Charge accumulates in the pixels in a linear fashion. Therefore, the monitor update period could be reduced to show a more linear increase of brightness of observed fluorescence. In some cases, it may be desirable to have more of a stepped visual image, as shown in FIG. 3. When the charge integration period ends, the accumulated charge is then released or dumped from the pixels, and a new charge integration period begins. Thus, the example of FIG. 3 shows the brightness of an image being repeated in a similar pattern between three and six seconds. Thus, it can be seen that the capability to view observed fluorescence within a cell sample is greatly enhanced by use of an imager having variable charge integration capability which may overcome low fluorescence of a particular cell sample.

Figure 4:
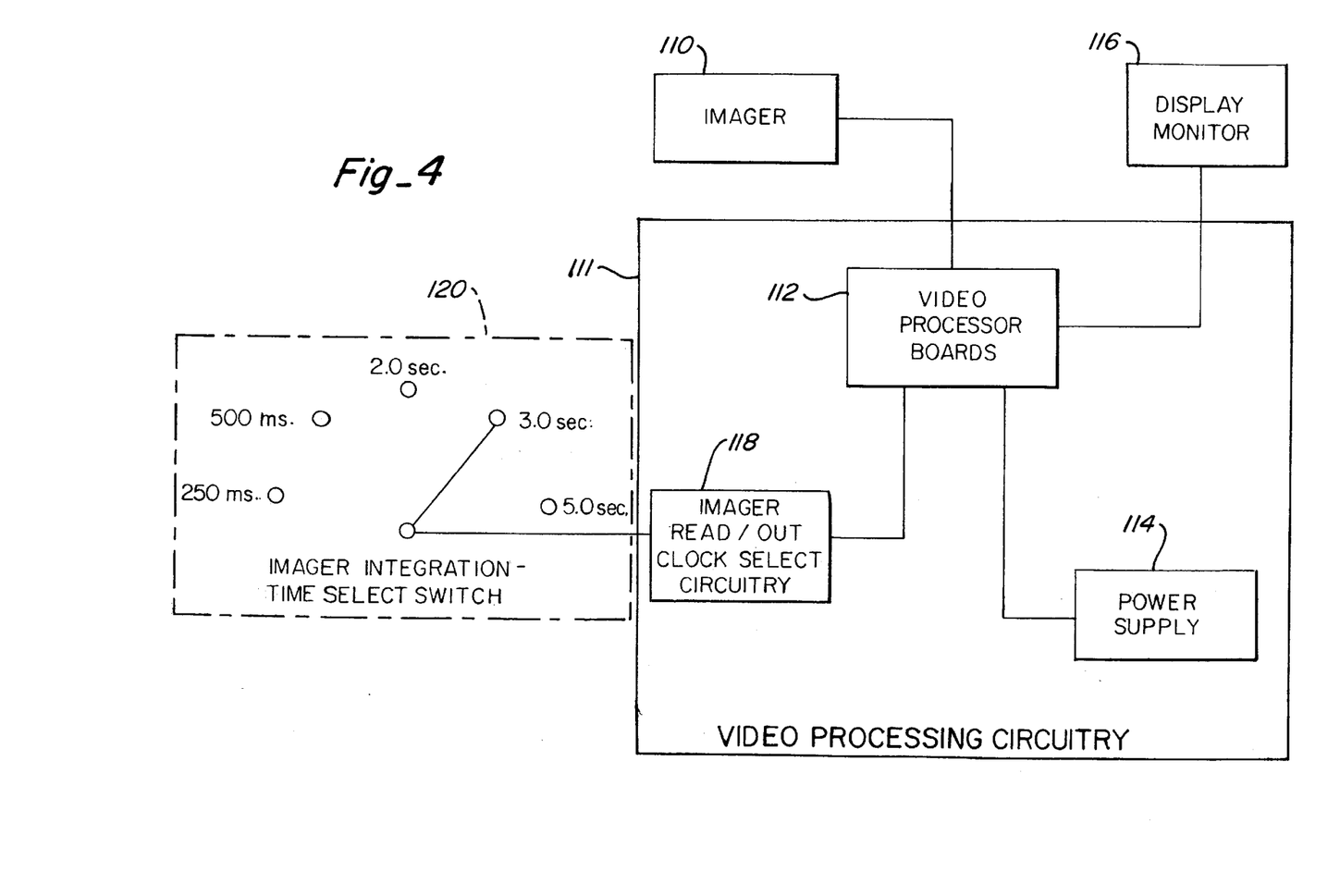
FIG. 4 is a schematic diagram illustrating incorporation of variable charge integration capability with an imager.

FIG. 4 is a schematic diagram of an imager and its processing circuitry which incorporate variable charge integration capability. An imager 110 is coupled to its video processing circuitry 111. The video circuitry 111 includes various video processor boards 112, and a power supply 114. Examples of an imager and video processing circuitry which may be used, as mentioned above, are those shown in my previous U.S. Pat. Nos. 5,986,693 and 5,929,901. In short, the imagers disclosed therein are CMOS type imagers which may be configured in multiple embodiments. In order to incorporate variable charge integration capability, imager readout clock select circuitry 118 is added which communicates with one or more of the video processor boards 112. An imager integration time select switch 120 is provided enabling an operator to manually select the desired integration period. As shown, the integration periods may be periods of less than one second, or more than one second. FIG. 4 illustrates a situation in which an operator has chosen a three-second integration period, resulting in an image being produced, as explained in FIG. 3. As the cell culture is observed by the imager 110, the imager will accumulate charge based upon the selected integration period. The image is viewed on the display monitor 116. As also discussed above, the monitor update period can also be adjusted to provide more or less of a stepped brightness image. The operator would then adjust the charge integration period to obtain the most desirable image of the cell culture enhancing observed fluorescence.

It should be understood that the imager 110 may be used in conjunction with the optics of a fluorescence microscope. Many fluorescence microscopes today also have miniature cameras which are used to record images observed by the fluorescence microscope. Thus, the imager 110 could replace the miniature camera or imager used on commercially available fluorescence microscopes. Also, it shall be understood that an endoscope which may be used in fluorescence guided endoscopy may also incorporate variable charge integration capability in order to enhance the ability to find and evaluate fluorescing cells. Thus, the use of variable charge integration capability has multiple benefits not only in viewing cells which have been removed from a body, but also to view cells in the body which may undergo some treatment or surgical procedure, and are to be located by fluorescence guided endoscopy.

It should also be understood that the collection of cells by the minimally/non-invasive methods discussed below may result in an extremely large number of cells being collected. For example, a specimen submitted from the uterine cervix collected by use of the cytology brush explained below, on the average, collects approximately 5 million cells. A careful manual examination of 5 million cells would take several days. Accordingly, in instances such as these where there are such a large number of cells, the first observation step at block 20 would be conducted by using several slides and observing them in the fluorescence microscope. If no fluorescing cells were found, the remainder of the specimen can then be processed through the flow cytometer. As desired, a FACS could also be conducted.

Depending upon the size of the sample which is taken from the body, the collected cells within the specimen could be processed on a standard flow cytometer even prior to initial observation under the fluorescence microscope. In the case of large volumes of fluid contained within a cell culture, such as one would obtain on a screen for uterine cervix or colon cancer, a flow cytometer can process large volumes of cells in a very short period of time. Commercially available flow cytometers may be used. Manufacturers of such devices include Coulter, Becton-Dickenson, and Cytomation. As well understood in the art, flow cytometry involves the suspension of individual cells in a solution, then moving the cells through a tubular system which only allows one cell at a time to flow. The cells pass through a chamber in the system where there is a selection of lasers of selected different frequencies of light to conduct a number of measurements to include cell counts, cell measurements as to overall size and other parameters. As applied to the method of this invention, the flow cytometer would have a selection of lasers which provide light to match the excitation frequency of the particular compound used to produce fluorescence in the cell sample. By this fluorescent tagging, the flow cytometer is able to accurately count the number of cells which fluoresce. In order to actually separate fluorescing versus non-fluorescing cells, the FACS must be conducted. The FACS involves the inducement of a charge (positive or negative) on the cell surface of each cell which passes through the flow cytometer. By this induced charge, the fluorescing cells are separated from non-fluorescing cells. Accordingly, the fluorescing cells would be placed into a separate container from the non-fluorescing cells. As discussed above, this concentrated sample of fluorescing cells makes viewing easier under a fluorescence microscope, and for easier photographing of the fluorescing cells. Because the use of a flow cytometer and the additional step of conducting a FACS involves the use of sophisticated and fairly expensive equipment, in most cases, it is desirable first to attempt to locate fluorescing cells by simply viewing them under a fluorescence microscope. However, it shall be understood that the methods of this invention are not limited to any particular sequence in terms of using a flow cytometer, a fluorescence microscope, or conducting a FACS. Thus, it is conceived within the spirit and scope of this invention that a FACS could be conducted immediately after the cell sample was centrifuged. However, since the great majority of tests conducted will yield a conclusion of no cancer, it is not advisable to immediately to move to either flow cytometry or conducting a FACS without first manually observing the cell sample through a fluorescence microscope. The capabilities of flow cytometers and fluorescence activated cell sorters are well known to those trained in the field.

As also shown in FIG. 1, introduction of the desired chemical compound for purposes of creating fluorescing cells can alternatively be achieved by introducing the compound to the patient prior to cell collection. This option is illustrated at block 11. As discussed above, the compound 5-ALA may be introduced to the patient orally, topically, or parenterally. The other compounds listed may only be given parenterally or topically.

The collected cells may be also placed in culture for observation over a longer period of time. In general, normal non-malignant cells will survive a much shorter period of time in comparison to malignant or neoplastic cells. This extended observation of the collected cells can be used as a confirmative test of the initial screening diagnosis.

Generally speaking, individual physician offices do not have fluorescence microscopes or other equipment which would be used to analyze the cells in the cell cultures. Accordingly, the cell cultures would be transported to a regional laboratory for examination by a laboratory technician and a physician. These individuals now perform standard screenings for conventional Pap smears and other cancer screening procedures.

As disclosed in Kennedy, et al., U.S. Pat. No. 5,211,938, 5-ALA is a significantly different compound compared to standard porphyrins in that it, by itself, 5-ALA is not a fluorescent marker, but is a precursor to a fluorescent marker, namely, protoporphyrin IX. When 5-ALA is administered, it enters a metabolic pathway within the cell and is converted to PPIX, which is an immediate precursor of heme. 5-ALA may be administered orally, topically, or by parenteral administration. 5-ALA is taken up by virtually all nucleated cells, and quickly enters into the "heme" synthesis pathway, eventually resulting in the transformation into PPIX. In non-malignant cells, the process is blocked by a built-in cellular feedback mechanism which effectively stops all PPIX formation. However, the feedback mechanism in malignant cells and those in rapid cell division (characteristic of many pre-malignant cells) is not operational, and PPIX is produced in significant quantities. 5-ALA is available from a manufacturer, Sigma Chemical Co., St. Louis, Mo. At the present time, 5-ALA is sold as a reagent worldwide, and not as a USFDA (Food and Drug Administration) approved drug; however, this may change since applications are in process to use 5-ALA in phototherapy.

Flow cytometers may also be used not only to count fluorescing cells, but also to measure various dimensions of cells including overall cell diameter, nuclear size, chromatin material in nucleus, cytoplasmic structures such as mitochrondia, and others. Cells may thus be sorted on the basis of overall cell size. Flow cytometers can also be programmed to count cells of a specific size, and provide overall counts of such cells in a total specimen. A flow cytometer can also be programmed to sort out and tabulate data on any type of cell from a whole host of cells in various cell suspensions. It is also understood by those skilled in the art that flow cytometers can do other sophisticated studies on the cells such as ploidy studies to determine the chromatin content of the nuclei (diploid cells have the correct number and size of chromosomes while aneuploid cells are those that have significant alterations in chromosome content). These very exacting measurements can be done at rates of thousands of cells per second.

In some circumstances, it may be necessary to provide some pre-separation of the collected cells. For example, based upon the collection techniques discussed above, some cells will be removed in clumps or sheets of cells. In order to ensure that these clumps or sheets of cells are completely exposed to the compound used as the fluorescent marker, the cells must be separated. Well known laboratory procedures exist for separation of these clumps or sheets of cells through use of certain enzymes, chelating agents, and even mechanical separation by high speed centrifugation followed by dilution in low viscosity solutions. These methods of cell "disaggregation" are well known in cell sorting laboratories.

Once the fluorescing cells are identified, the cells can be saved for further examination by a trained pathologist. Ultimately, a pathologist makes a diagnosis as to the presence of a malignancy. If it is determined that the collected cells are malignant, the prior art methods may then be used to locate and remove the tumor (such as described in Kennedy, et al., U.S. Pat. No. 5,211,938), or the tumor may then be located and removed by fluorescence guided endoscopic surgery, utilizing endoscopes and surgical devices under guidance of fluorescence. If it is determined that open surgery is required to remove a tumor, fluorescence assisted surgery can also be conducted under these circumstances wherein the surgeons utilize headlights capable of delivery of tuned frequencies of light, and other light emitting equipment may be used, such as retractors, probes, and dissectors with built-in illumination.

As mentioned briefly above, fluorescence-assisted surgery can also be enhanced by providing an endoscope utilizing a CMOS or CID imager which has variable charge integration capability. As with observance of a cell culture, the ability of a surgeon to view a cancerous growth inside the patient can be enhanced by choosing an integration period which greatly expands the imaging sensitivity of the endoscope. It is not well recognized by many working in the cancer detection field that PPIX has a relatively "long tail" on the fluorescence curve that extends out to 900 nanometers and, in some circumstances, to 1400 nanometers. The capability exists with the method of this invention to stimulate a tumor fairly deep into the tissue of a patient with an excitation frequency of 635–650 nanometers. Penetration can be to a depth of 6–7 cm. Thus, for breast cancer or other cancers, which can be as deep as 6–7 cm, use of an imager with variable charge integration capability would allow a physician to externally view a cancerous growth as deep as 6–7 cm without any required interventional procedures. The faint or slight amount of fluorescence which might not be observable through a CCD imager can be enhanced by using a CID or CMOS imager modified with variable charge integration capability, resulting in readily observable fluorescence. Thus, in every conceivable aspect of endoscopy and cancer screening, use of an endoscope having a variable charge integration capability is advantageous for finding a cancerous growth.

In accordance with another method of this invention, fluorescence guided endoscopy can be conducted wherein the endoscope incorporates variable charge integration capability to enhance the surgeon's capability to find and diagnosis cancerous tissue. One example of this might be fluorescence endoscopy to find colon cancer. Once the patient has been administered 5-ALA or another similar compound, the surgeon would conduct the endoscopic procedure looking for fluorescing colon tissue. As the surgeon conducts the endoscopic procedure, the charge integration periods could be adjusted to maximize observable fluorescence. In some cases, it may be very difficult for the surgeon to find all fluorescing tissues within the colon. By using the variable charge integration capability incorporated within the endoscope, the surgeon is more capable of finding each and every fluorescing groups of tissue within the colon to make a proper diagnosis. Examples of endoscopes which may be used in the endoscopic procedure are those shown in my previous patents, U.S. Pat. Nos. 5,986,693 and 5,929,901. The endoscopes disclosed therein can be modified in accordance with the schematic diagram of FIG. 4 enabling a surgeon to adjust the charge integration periods. Also, light delivery to the surgical site can be chosen from a desired frequency of light corresponding to the excitation frequency of the compound administered to the patient.

The methods of this invention primarily utilize cells which normally desquamate from the various surfaces of the body, both internal and external, thus their removal by non-invasive means does not result in undue patient trauma. These non-invasive cell collection methods accelerate the release of such cells from the surfaces of the tumor mass, and then, as described above, are collected and analyzed.

Figure 2A:
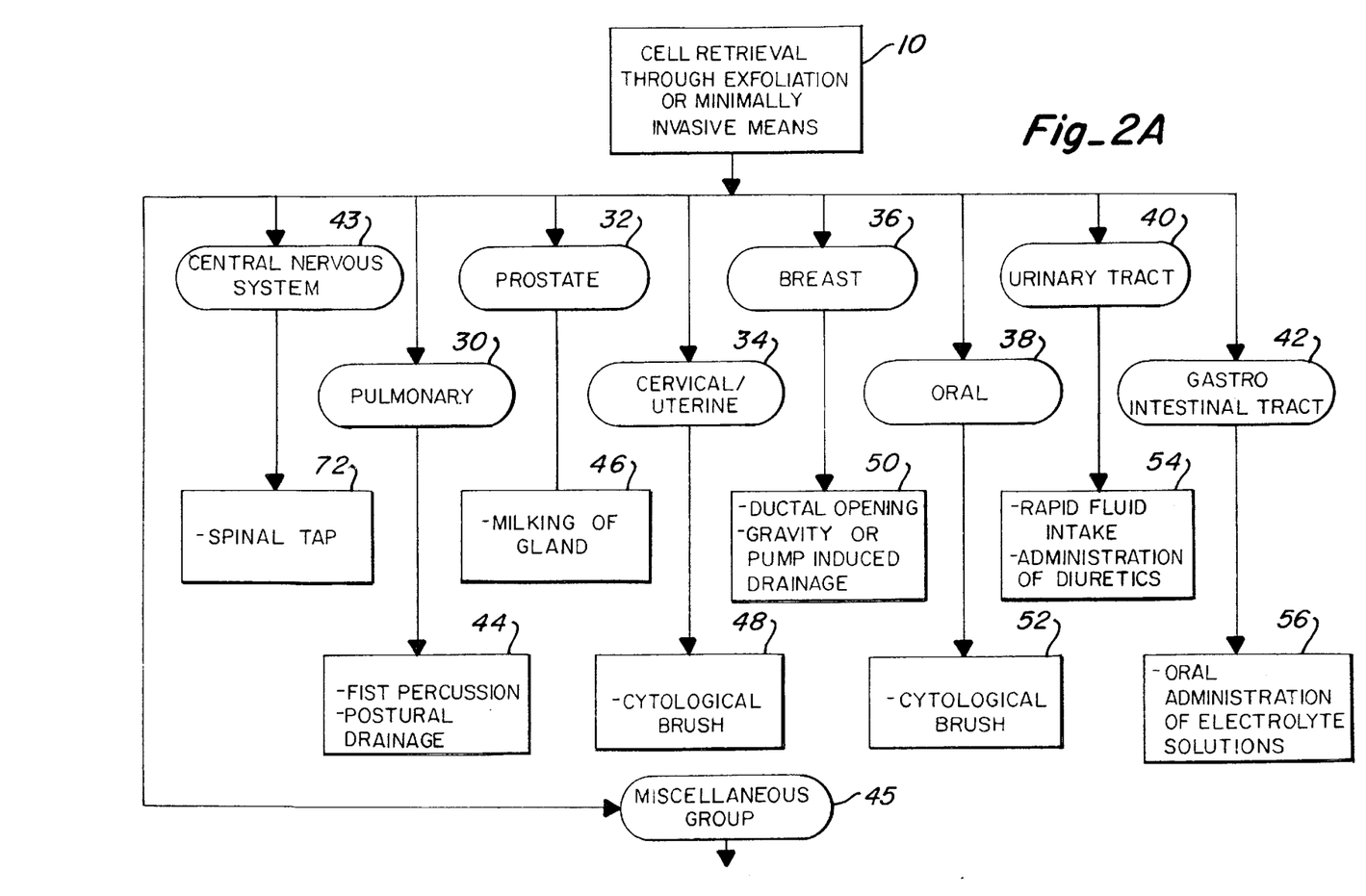
FIG. 2 is an organizational diagram illustrating both the types of cells which may be exfoliated or collected according to the cell collection techniques of this invention, and the major steps in the various cell collection techniques.
Figure 2B:
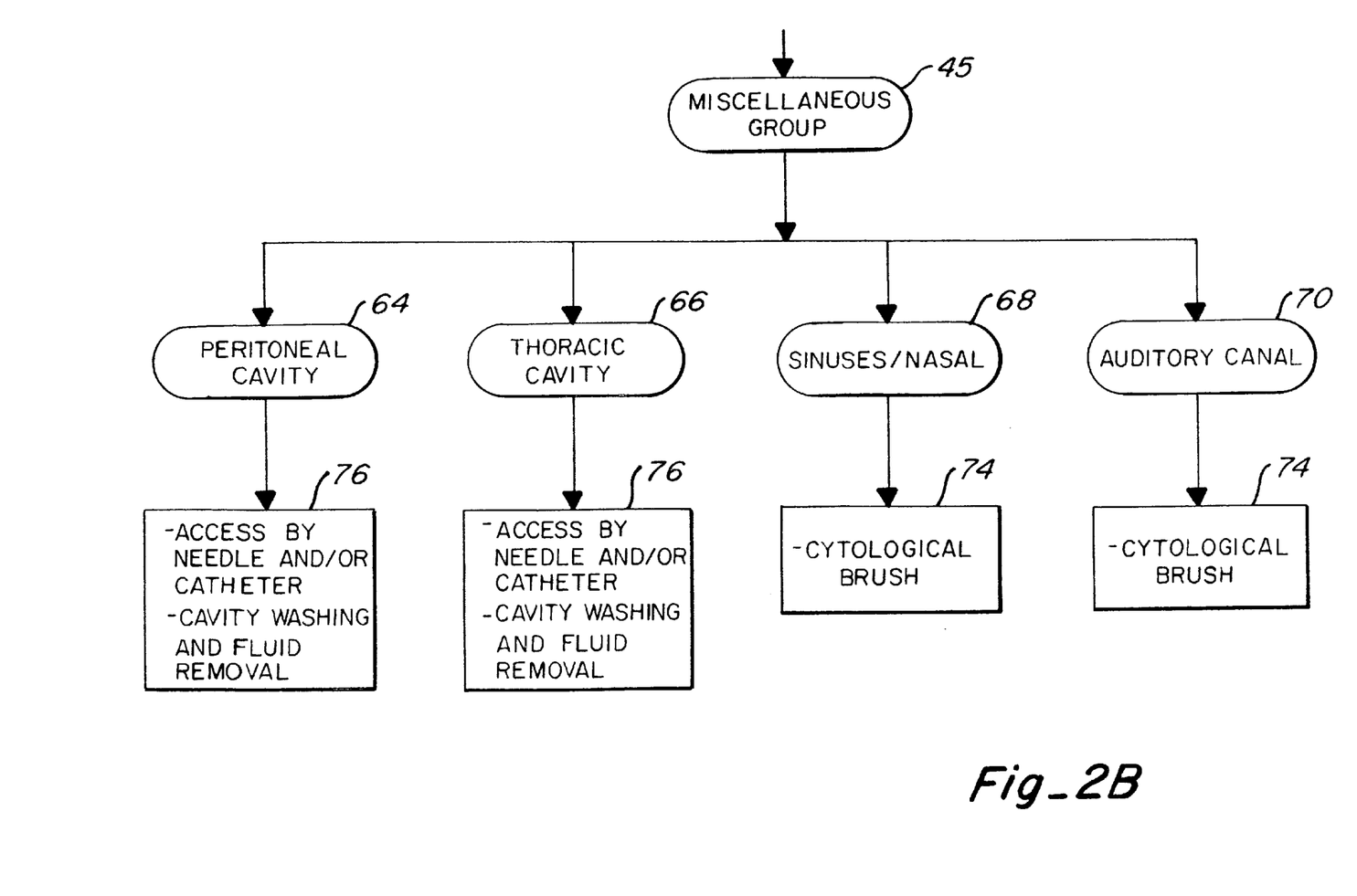

FIG. 2 illustrates an organizational diagram of the types of cells which may be removed according to these non-invasive and minimally invasive methods, and also shows the major steps or actions which are used to collect the types of cell. As shown, cell collection 10 may be achieved with cells from the pulmonary system 30, prostate gland 32, cervical/uterine area 34, breast 36, oral areas 38, urinary tract 40, gastrointestinal tract 42, central nervous system 43, and a miscellaneous group 45.

The specific types of cells which may be exfoliated are as follows:

1. Pulmonary system 30—trachea, bronchi, bronchioli, and alveoli.
2. Prostate gland 32—seminal vesicles and ejaculatory ducts.
3. Cervical/uterine area 34—uterus, cervix and uterine cavity cells.
4. Breast 36—ductal carcinoma cells.
5. Oral 38—all cell types exposed in the mouth to include cheek lining, tongue, floor and roof of the mouth, gums and throat.
6. Urinary tract 40—kidney pelvis, calyces, ureters, urinary bladder, and urethra.
7. Gastrointestinal tract 42—esophagus, stomach, small intestine, and large intestine (colon).
8. Central nervous system 43—ventricles and meninges.

In addition to the general cell categories discussed above, there are other cells within the body which may be removed by the non-invasive or minimally invasive techniques. This miscellaneous group is shown as group 45 which includes cells from the peritoneal cavity 64 such as liver, pancreas, ovaries, and other peritoneal cells, and cells from the thoracic cavity 66 such as pleurocentesis cells. Also included from this miscellaneous group are cells within the sinus and nasal system 68 and auditory canal 70.

Now, a discussion will follow which more particularly points out the non-invasive and minimally invasive techniques of cell collection for each of the groups of cells.

Block 44 lists the major actions conducted in collecting cells from the pulmonary system 30. As shown, this non-invasive collection technique includes fist percussion while a patient is placed in a postural drainage position, and then postural drainage allows cell laden respiratory fluid to be captured. Sputum, by itself, does not generally contain pulmonary cells which come from the lining of the air ducts within the lung (bronchi and alveoli cells). Therefore, the postural drainage in conjunction with the fist percussion helps to dislodge pulmonary cells to create a cell laden fluid with bronchi, alveoli, and the other cells listed above. The patient is placed on the edge of a bed or other horizontal surface with the hips and legs horizontal, and the chest and head hanging down to the floor. This postural drainage position allows secretions from the alveoli, bronchi, and trachea to flow by gravity through the trachea toward the mouth. Repeated fist percussion over the entire chest wall helps to continue the dislodgement of cells and to continue the flow through the trachea to the mouth. Coughing at intervals also allows for collection of large numbers of cells during postural drainage.

For exfoliation of prostate cells 32, the non-invasive collection method is achieved simply by "milking" the prostate gland. This is shown at block 46. A physician would simply conduct a digital rectal examination to determine the status of the gland. The gland is "milked" by squeezing the gland to express contained fluids. These fluids are carried by the ductal system to the urethra via the seminal vesicles and ejaculatory ducts.

For exfoliation of cervical and uterine cells 34, non-invasive collection can be carried out by use of a cytology brush, shown at step 48. One example of a cervical collection brush which can be used is disclosed in my earlier U.S. Pat. No. 4,762,113. The cytology brush disclosed in this patent has proven to be superior to standard cytological brushes in its ability to collect the necessary quantity of cells.

For exfoliation of cells from the breast 36, the patient is placed in a face down position with both breasts dropping down through apertures in an examination table top. This allows both breasts to hang, unsupported, through the table top. The ductal system of the breasts can then be opened by use of a product such as "Seruminex™." Gravity allows fluids retained within the breast ductal system to drain out through the ducts in the nipple. To accelerate fluid removal, a commercially available breast pump could be used, such as that used by nursing mothers. This non-invasive method is shown at block 50.

In order to obtain cells from the mouth or throat area, a cytological brush may be used which brushes the suspicious areas. This non-invasive technique is shown at block 52. The cervical collection brush mentioned above is also ideal for use in removal of cells in the mouth and throat.

In order to exfoliate cells from the urinary tract 40, rapid oral fluid intake in conjunction with administration of diuretics such as Lasix™ results in cell exfoliation from the transitional cell linings of the urinary tract. Fluids are collected from the urethra, and some fluids may be washed out further by the act of urination. This very rapid flow, occurring at the level of the renal pelvis and continuing through the ureters, bladder, and urethra will dislodge cells in large quantities. The cells can then be collected, concentrated by centrifugation, and preserved in the cell transport media of the cell culture. This method is shown at block 54.

In order to collect cells from the gastrointestinal tract 42, lavage cytology is utilized by first giving the patient an orally administered balanced electrolyte solution. The solution may include drugs which increase bowel evacuation, such as biscodyl, colyte, and golytely. This first application of an electrolyte solution induces a cleansing wash of the bowel to remove fecal materials. Then, an additional orally administered electrolyte solution can be given to the patient to produce a clear anal effluent for cytological evaluation. This clear fluid contains thousands of cells, and if a malignancy exists, cancer cells will be washed out with the large volume of fluid. This technique is shown at block 56.

Cells can be collected from the central nervous system 43 by conducting a "tap" of the spinal canal with a syringe and needle used in standard spinal tap procedures. Thus, for this type of cell collection, non-invasive means for cell exfoliation is not possible. This technique for removal of cells from the central nervous system 43 is shown at block 72.

Non-invasive means are also not available for removal of cells from both the chest (thoracic) cavity 66 and the peritoneal cavity 64. A minimally invasive means of cell collection for these types of cells may be achieved by utilizing a syringe and needle or using a peritoneal lavage catheter. A syringe and needle or a catheter inserted through a needle is placed in the cavity. Fluids are introduced into the cavity to dislodge cells, and then the cell laden fluid is removed from the cavity for collection. This involves the use of normal saline irrigations via the catheter (a wash of peritoneal cells). As necessary, the cells are centrifuged and immediately placed in the cell transport media. This technique is identified as blocks 76 in FIG. 2.

To induce exfoliation for cells in the auditory canal 70 or the nasal area and sinus passages 68, a cytologic brush may be used. The brush is inserted into the ear or nose and placed in contact with the targeted area. This method is shown at blocks 74 of FIG. 2. The cervical cytological brush mentioned above may also be used to collect cells from these areas.

In summary, the methods of this invention are extremely effective in detecting early or latent cancer in asymptomatic patients. The techniques of cell collection disclosed herein allow for screening of cancer from virtually every site in the body at minimal trauma to the patient and at minimal cost.

One very clear example of the advantages of the methods of this invention over standard cancer screening procedures is with relation to screening for prostate cancer. The typical procedure for prostate cancer screening is for the urologist to conduct a digital rectal examination which amounts to a "feel" of the prostate for areas of increased hardness within the gland. There are very many other reasons for hard lumps in the prostate gland including stones, fibrosis from prior infection, cysts, and infarction from loss of blood supply to a given segment of the gland. In addition, the urologist may order a study of acid phosphatase levels (a substance which may be elevated in the presence of a prostate cancer), and may order a study of prostate specific antigen levels (PSA) levels. Pelvis and abdominal x-rays may be used to determine if there are signs of bone metastasis. Ultrasound studies may be used to determine if there are any suspicious areas in the prostate gland. Each of the foregoing studies are presumptive tests, but none are absolutely diagnostic of prostate cancer. Even when these tests are performed, multiple needle biopsies are done which attempt to find cancerous areas in the gland. In short, the above-identified procedures are costly, can cause trauma to the patient, and do not necessarily provide for an early diagnosis. By comparison, the methods of this invention are a relatively absolute diagnosis of a cancer. Although a pathologist may still wish to confirm the results of the screening tests of this invention, the screening tests of this invention greatly eliminate many costly procedures and greatly streamlines early cancer diagnosis.

This invention has been described in detail with reference to particular embodiments thereof, but it will be understood that various other modifications can be effected within the spirit and scope of the invention.

What is claimed is:

1. A method of cancer screening comprising the steps of:
   collecting targeted cells from the human body;
   placing the collected cells in a cell culture media;
   introducing a chemical compound to the collected cells;
   maintaining exposure of the collected cells to the chemical compound to allow the collected cells to adequately interact with the chemical compound;
   keeping at least some of the collected cells alive during said maintaining step to ensure adequate interaction;
   stimulating the collected cells by a selected range of frequency of light to cause pre-malignant and malignant cells to fluoresce;
   viewing the collected cells with an imager to determine if fluorescence occurs in the collected cells indicating the presence of cancer; and
   adjusting a charge integration period of the imager to maximize observable fluorescence.

2. A method, as claimed in claim 1, further including the step of:
   conducting long-term cell observations to further distinguish pre-malignant and malignant cells from normal cells.

3. A method, as claimed in claim 1, further including the step of:
   photographing collected cells which fluoresce as documentation for diagnosis of a malignancy.

4. A method, as claimed in claim 1, further including the step of:
   conducting flow cytometry to selectively count collected cells.

5. A method, as claimed in claim 1, further including the step of:
   conducting fluorescence activated cell sorting to selectively sort collected cells.

6. A method, as claimed in claim 1, wherein:
   said chemical compound is 5-ALA.

7. A method of cancer screening achieved by screening cells previously removed from the body, said method comprising the steps of:
   placing collected cells in a cell culture media;
   introducing a chemical compound to the collected cells;
   maintaining exposure of the collected cells to the chemical compound to allow the collected cells to adequately interact with the chemical compound and to keep at least some of the cells alive;
   stimulating the collected cells by a selected range of a frequency of light to cause premalignant and malignant cells to fluoresce;
   viewing the collected cells with an imager to determine if fluorescence occurs in the collected cells indicating the presence of cancer; and
   adjusting a charge integration period of the imager to maximize observable fluorescence.

8. A method, as claimed in claim 7, further including the step of:
   conducting long-term cell observations to further distinguish pre-malignant and malignant cells from normal cells.

9. A method, as claimed in claim 7, further including the step of:
   photographing collected cells which fluoresce as documentation for diagnosis of a malignancy.

10. A method, as claimed in claim 7, further including the step of:
    conducting flow cytometry to selectively count collected cells.

11. A method, as claimed in claim 7, further including the step of:
    conducting fluorescence activated cell sorting to selectively sort collected cells.

12. A method, as claimed in claim 7, wherein:
    said chemical compound is 5-ALA.

13. A method of cancer screening comprising the steps of:
    administering a chemical compound to a patient, said chemical compound being one for use as a fluorescent marker which interacts with a targeted group of cells;
    collecting targeted cells from the body;
    placing the collected cells in a cell culture media;
    maintaining exposure of the collected cells to the chemical compound to further interact with the chemical compound;
    keeping at least some of the collected cells alive during said maintaining step to ensure adequate interaction;
    stimulating the collected cells by a selected range of a frequency of light to cause premalignant and malignant cells to fluoresce;
    viewing the collected cells with an imager to determine if fluorescence occurs in the collected cells indicating the presence of cancer; and
    adjusting a charge integration period of the imager to maximize observable fluorescence.

14. A method, as claimed in claim 13, further including the step of:
    conducting flow cytometry to selectively count collected cells.

15. A method, as claimed in claim 13, further including the step of:
    conducting fluorescence activated cell sorting to selectively sort collected cells.

16. A method of cancer screening comprising the steps of:
    administering a chemical compound to a patient, said chemical compound being one for use as a fluorescent marker which interacts with a targeted group of cells;
    conducting an endoscopic procedure by use of an endoscope having a variable charge integration imager, to locate the targeted group of cells;
    stimulating the targeted group of cells by delivering a selected range of a frequency of light to cause premalignant and malignant cells to fluoresce from the targeted group of cells;
    viewing the targeted cells with the imager of the endoscope to determine if fluorescence occurs in the targeted group of cells indicating the presence of cancer; and
    adjusting a charge integration period of the imager to maximize observable fluorescence.

17. A method, as claimed in claim 16, wherein:
    said chemical compound is 5-ALA.

* * * * *